United States Patent [19]

Wilson

[11] Patent Number: 5,914,405

[45] Date of Patent: Jun. 22, 1999

[54] PROCESS FOR PREPARING 3-SUBSTITUTED INDAZOLES

[75] Inventor: Thomas Michael Wilson, Speedway, Ind.

[73] Assignee: Eli Lilly and Company, Indianapolis, Ind.

[21] Appl. No.: 09/163,613

[22] Filed: Sep. 30, 1998

Related U.S. Application Data

[63] Continuation-in-part of application No. 08/946,263, Oct. 7, 1997.

[51] Int. Cl.$^6$ .................................................. C07D 401/12
[52] U.S. Cl. .......................................... 546/199; 548/362.5
[58] Field of Search ........................... 546/199; 548/362.5

[56] References Cited

U.S. PATENT DOCUMENTS 5,654,320   8/1997   Catlow et al. ........................... 546/148

OTHER PUBLICATIONS

*Journal of the American Chemical Society*, 79, 5242 (1957).
*Heterocycles*, 41 (7), 1471–1478 (1995).
*Bulletin of the Korean Chemical Society*, 15 (2), 97–98 (1994).
*Synthesis*, 982–983 (1984).

Primary Examiner—Robert W. Ramsuer
Attorney, Agent, or Firm—Gilbert T. Voy

[57] ABSTRACT

The invention provides a method of preparing compounds of formula I and VIII:

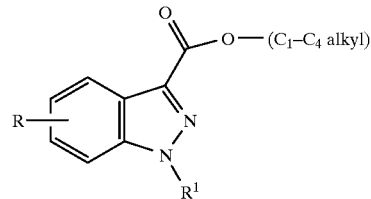

I

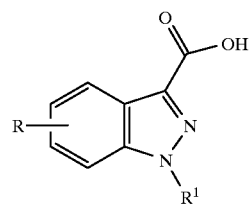

VIII which are useful intermediates to compounds that are used as antagonists and partial agonists for the serotonin receptor 5-HT$_4$.

12 Claims, No Drawings

PROCESS FOR PREPARING 3-SUBSTITUTED INDAZOLES

This application is a Continuation In Part of U.S. application Ser. No. 08/946,263, filed Oct. 7, 1997, the teachings of which are herein incorporated by reference.

FIELD OF THE INVENTION

The present invention relates to chemical processes. More particularly, the present invention concerns a process for preparing indazole compounds.

BACKGROUND OF THE INVENTION

Processes in the brain and other organs involving serotonin as a neurotransmitter have been a major field of pharmacological research for some decades. A large number of processes which depend on serotonin have been identified, and numerous therapeutic compounds which affect such processes are in widespread use. More than a dozen receptors which are acted upon by serotonin have been identified. Some of the receptors' physiological mechanisms have been identified, and others are still the subject of extended and active research. One of the more recently identified serotonin receptors is known as 5-HT$_4$. Bockaert J., Fozard J., Dumuis A., et al., "The 5-HT$_4$ Receptor: A Place in the Sun", *Trends Pharmacol. Sci.*, 13, 141, 1992. Therapeutic methods making use of the 5-HT$_4$ receptor have been held back by the lack of compounds which affect the 5-HT$_4$ receptor without substantial effect at other receptors.

Recently, a series of new pharmaceutical agents which have high affinity and selectivity at the 5-HT$_4$ receptor have been identified and disclosed in U.S. Pat. No. 5,654,320, the entirety of which is herein incorporated by reference. A key intermediate to those compounds, and compounds disclosed within which also have high affinity and selectivity at the 5-HT$_4$ receptor, is the indazolic ester of formula I:

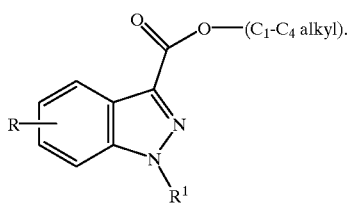

I

Compared to the many synthetic routes leading to compounds of formula I (See e.g. *Heterocyclic Compounds*, Vol. 5, R. C. Elderfield, Ed., John Wiley & Sons, New York, 1957, pp. 162–193), dehydrogenation of compounds of formula II:

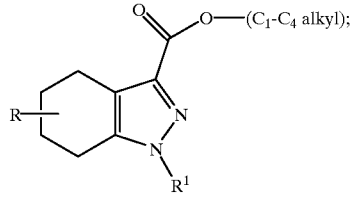

II is most direct. However, the following considerations limit the practical utility of this synthesis: extreme reaction conditions are required for dehydrogenation (palladium on carbon in decalin at 200° C. for 48 hours), and overall yields are low (58% when R and R$^1$ are both hydrogen, and the C$_1$–C$_4$ alkyl group is ethyl). F. Piozzi, A. Umani-Ronchi, L. Merlini, *Gazz.Chim.Ital.* 95, 814 (1965), and J. P. Burnett, C. Ainsworth, *J. Org. Chem.* 23, 1382, (1958).

A more recent synthesis published in 1984 provided access to the indazole ring system by the route shown below where R$^2$ is hydrogen or phenyl:

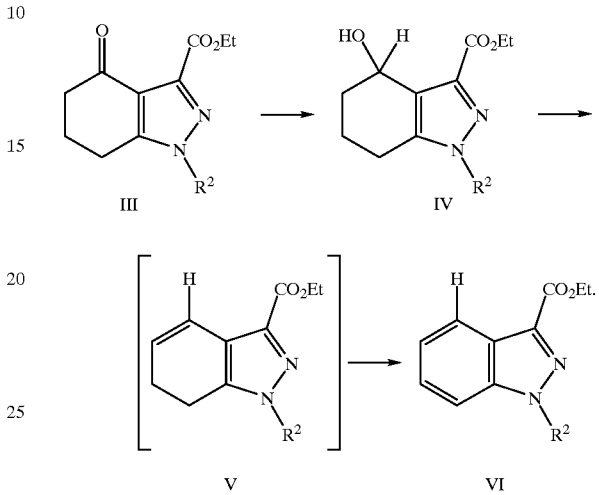

The above sequence represents a reduction of a ketone of formula III, a dehydration of the resulting compound IV, followed by an in situ aromatization of intermediate V. This two step synthesis is performed at 100° C. in a dioxane solution of p-toluenesulfonic acid in the presence of palladium on carbon providing product at yields up to 73%. La Rosa, C., Dalla Croce, P., *Synthesis,* 982, (1984). The lower reaction temperatures can be attributed to the intermediate of formula V which is unstable toward oxidation.

This newer synthesis suffers in three respects. First, substitution at the 4 position of the indazole system is limited to hydrogen. Secondly, the necessity of performing the dehydration reaction in the presence of an acid at elevated temperatures could be incompatible with certain functional groups e.g. a hydroxyl group. Lastly, yields for the reaction have much room for improvement. An improvement over the prior art would be a process that does not require extreme temperatures or acid, is higher yielding, and is not dependent upon a 4-keto intermediate.

SUMMARY OF THE INVENTION

The invention provides a method of preparing compounds of formula I:

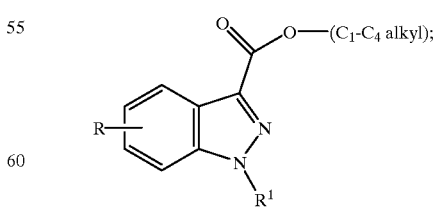

I wherein:

R is hydrogen, C$_1$–C$_4$ alkyl, hydroxy, C$_1$–C$_4$ alkoxy, C$_1$–C$_4$ alkylthio, cyano, trifluoromethyl, carboxamido, mono or di(C$_1$–C$_4$ alkyl) carboxamido;

$R^1$ is hydrogen, $C_1$–$C_6$ alkyl, $C_3$–$C_6$ cycloalkyl, or substituted $C_3$–$C_6$ cycloalkyl;

which includes the step of:

heating a mixture of a compound of formula VII:

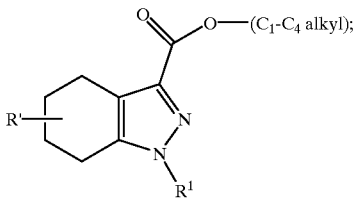

VII wherein:

R' is oxo, hydrogen, $C_1$–$C_4$ alkyl, hydroxy, $C_1$–$C_4$ alkoxy, $C_1$–C4 alkylthio, cyano, trifluoromethyl, carboxamido, mono or di($C_1$–$C_4$ alkyl) carboxamido;

a substituted benzene solvent, and an oxidation catalyst at a temperature between 110° C. and the reflux temperature of the mixture to provide a compound of formula I.

DETAILED DESCRIPTION OF THE INVENTION

In the present document, all expressions of concentration, percent, ratio and the like will be expressed in weight units unless otherwise stated, except for mixtures of solvents which will be expressed in volume units. All temperatures not otherwise stated will be expressed in degrees Celsius.

In the general formulas of the present document, the general chemical terms have their usual meanings. For example, the term "$C_1$–$C_3$ alkyl" refers to methyl, ethyl, propyl, and isopropyl. The term "$C_1$–$C_4$ alkyl" includes those encompassed by $C_1$–$C_3$ alkyl in addition to n-butyl, s-butyl, and t-butyl. The term "$C_1$–$C_6$ alkyl" includes those encompassed by $C_1$–$C_4$ alkyl in addition to pentyl, pent-2-yl, pent-3-yl, 2-methylbutyl, 2-methylbut-2-yl, 3-methylbut-2-yl, 3-methylbutyl, 2,2-dimethylpropyl, hexyl, hex-2-yl, hex-3-yl, 2-methylpentyl, 2-methylpent-2-yl, 2-methylpent-3-yl, 4-methylpent-2-yl 4-methylpentyl, 2,3-dimethylbutyl, 2,3-dimethylbut-2-yl, 2,2-dimethylbutyl, 3,3-dimethylbut-2-yl, and 3,3-dimethylbutyl. The term "$C_3$–$C_6$ cycloalkyl" refers to cyclopropyl, cyclobutyl, cyclopentyl, and cyclohexyl.

The term "$C_1$–$C_4$ alkoxy" refers to methoxy, ethoxy, propoxy, isopropoxy, n-butoxy, s-butoxy, and t-butoxy.

The term "$C_1$–$C_4$ alkylthio" refers to methylthio, ethylthio, propylthio, isopropylthio, n-butylthio, s-butylthio, and t-butylthio.

The terms "substituted $C_3$–C6 cycloalkyl", "substituted phenyl", and "substituted benzoyl" refer, respectively, to a cycloalkyl, phenyl, and benzoyl group substituted from 1 to 3 times with substituents selected independently from the group consisting of: halo, $C_1$–$C_4$ alkyl, hydroxy, $C_1$–$C_4$ alkoxy, $C_1$–$C_4$ alkylthio, cyano, trifluoromethyl, carboxamido, and mono or di ($C_1$–$C_4$ alkyl)carboxamido. The term "substituted benzene solvent" refers to a benzene ring substituted from 1 to 3 times independently at each occurrence with a $C_1$–$C_6$ alkyl group.

The term "halo" and "halide" refers to chloro, fluoro, bromo, and iodo.

The term "carbonyl activating group" refers to a substituent of a carbonyl that promotes nucleophilic addition reactions at that carbonyl. Suitable activating substituents are those which have a net electron withdrawing effect on the carbonyl. Such groups include, but are not limited to, alkoxy, aryloxy, nitrogen containing aromatic heterocycles, or amino groups such as oxybenzotriazole, imidazolyl, nitrophenoxy, pentachlorophenoxy, N-oxysuccinimide, N,N'-dicyclohexylisoure-O-yl, N-hydroxy-N-methoxyamino, and the like; acetates, formates, sulfonates such as methanesulfonate, ethanesulfonate, benzenesulfonate, or p-tolylsulfonate, and the like; and halides such as chloride, bromide, or iodide.

The term "suitable carbonyl activating reagent" refers to a reagent that converts the carbonyl of a carboxylic acid group to one that is prone to nucleophilic addition and includes, but is not limited to, such reagents as those found in *The Peptides*, Gross and Meienhofer, Eds., Academic Press (1979), Ch. 2, hereafter referred to as "*The Peptides*". Other carbonyl activating reagents include halogenating reagents such as benzeneseleninylchloride/aluminum chloride, thionyl bromide, thionyl chloride, oxalyl chloride, N-bromosuccinimide, N-iodosuccinimide, N-chlorosuccinimide, molecular chlorine, bromine, and iodine, and the like; alcohols such as nitrophenol, pentachlorophenol, and the like; amines such as N-hydroxy-N-methoxyamine and the like; acid halides such as acetic, formic, sulfonic, methanesulfonic, ethanesulfonic, benzenesulfonic, or p-tolylsulfonic acid halide, and the like; and compounds such as 1,1'-carbonyldiimidazole, benzotriazole, imidazole, N-hydroxysuccinimide, dicyclohexylcarbodiimide, and the like.

The term "amino protecting group" as used in this specification refers to substituents of the amino group commonly employed to block or protect the amino functionality while reacting other functional groups on the compound. Examples of such amino-protecting groups include the formyl group, the trityl group, the phtalimido group, the acetyl group, the trichloroacetyl group, the chloroacetyl, bromoacetyl, and iodoacetyl groups, urethane-type blocking groups such as benzyloxycarbonyl, 9-fluorenylmethoxycarbonyl ("FMOC"), and the like; and like amino protecting groups. The species of amino protecting group employed is not critical so long as the derivitized amino group is stable to the condition of subsequent reaction (s) on other positions of the molecule and can be removed at the appropriate point without disrupting the remainder of the molecule. Similar amino protecting groups used in the cephalosporin, penicillin, and peptide arts are also embraced by the above terms. Further examples of groups referred to by the above terms are described by J. S. Barton, "Protective Groups in Organic Chemistry", J.G.W. McOmie, Ed., Plenum Press, New York, N.Y., 1973, Chapter 2, and T. W. Greene, "Protective Groups in Organic Synthesis", John Wiley and Sons, New York, N.Y., 1991, Chapter 7 hereafter referred to as "*Barton*" and "Greene" respectively.

The term "hydroxy activating substituent" refers to a substituent that is singly bonded to an oxygen atom that makes the moiety as a whole, i.e. the group of the formula O-(hydroxy activating substituent), labile to displacement. Typical hydroxy activating substituents include, but are not limited to, p-tolunesulfonyl, phenylsulfonyl, trifluoromethylsulfonyl, isobutoxycarbonyl, acetyl, and the like.

The term "hydroxy activation reagent" refers to organic or inorganic acids, acid halides, and acid anhydrides that are capable of displacing a hydroxy group with a leaving group or converting a hydroxy group into a leaving group labile to base treatment and/or nucleophilic displacement. Typical hydroxy activation agents include, but are not limited to, p-tolunesulfonyl chloride, phenylsulfonyl chloride, trifluoromethylsulfonyl chloride, isobutyl chloroformate, acetyl chloride, thionyl chloride, phosphorus tribromide, and the like. Thionyl chloride or bromide and oxalyl chloride are also hydroxy activating agents.

The term "hydroxide base" refers to lithium, cesium, sodium, or potassium, calcium, and magnesium hydroxide.

The term "suitable thermodynamic base" refers to a base which is used to trap a proton(s) generated as a byproduct of a reaction or a base that provides a reversible deprotonation of an acidic substrate and is reactive enough to affect the desired reaction without significantly affecting any undesired reactions. Examples of thermodynamic bases include, but are not limited to, carbonates, bicarbonates, and hydroxides (e.g. lithium, sodium, or potassium carbonate, bicarbonate, or hydroxide), tri-($C_1$–$C_4$ alkyl)amines, or aromatic nitrogen containing heterocycles (e.g. pyridine).

The term "suitable kinetic base" refers to a base which provides a non-reversible deprotonation of an acidic substrate and is reactive enough to effect the desired reaction without significantly effecting any undesired reactions. Examples of kinetic bases include, but are not limited to, alkyl metals (e.g. n-butyl lithium, s-butyl lithium, and t-butyl lithium or ethyl magnesium bromide), metal amides such as lithium diisopropyl amide, metal alkoxides such as potassium t-butoxide, or metal hydrides (e.g. sodium, lithium, or potassium hydride).

The term "suitable solvent" refers to a solvent which is inert to the ongoing reaction and sufficiently solubilizes the reactants to effect the desired reaction. Examples of suitable solvents include but are not limited to, methylene chloride, chloroform, 1,2-dichloroethane, diethyl ether, acetonitrile, ethyl acetate, 1,3-dimethyl-2-imidazolidinone, tetrahydrofuran, dimethylformamide, toluene, chlorobenzene, dimethylsulfoxide, mixtures thereof, and the like.

The term "pharmaceutically acceptable salt" as used herein, refers to salts of the compounds of formula X which, at the doses administered, are substantially non-toxic to living organisms. Typical pharmaceutically acceptable salts include those salts prepared by reaction of the compounds of the formula X with a mineral or organic acid. Such salts are known as acid addition salts.

Examples of such pharmaceutically acceptable salts are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, γ-hydroxybutyrate, glycollate, tartrate, methanesulfonate, ethanesulfonate, propanesulfonate, naphthalene-1-sulfonate, napththalene-2-sulfonate, mandelate, and the like of a compound of formula X.

Compounds of formula I may be prepared by a novel process illustrated in Scheme 1 and 2 below where R, R', and $R^1$ are as described supra.

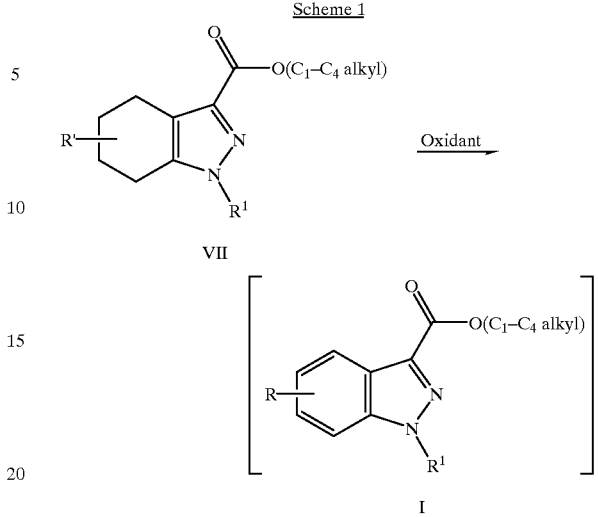

Scheme 1

Compounds of formula I may be prepared in a novel one step reaction from a compound of formula VII. The oxidation is typically run by heating a mixture of a compound of formula VII, dissolved or suspended in a substituted benzene solvent, in the presence of an oxidation catalyst, usually for from 12 to 48 hours. More preferably, the oxidation is run for from 20 to 40 hours and most preferably for from 22 to 26 hours. The reaction may be performed at a temperature between 110° C. and the reflux temperature of the mixture. More preferably, the reaction is performed at a minimum temperature of 140° C. Even more preferred is a minimum temperature of 170° C. It is most preferable to perform the reaction at the reflux temperature of the mixture. Suitable substituted benzene solvents include, benzene substituted from 1 to 3 times independently, preferably disubstituted, at each occurrence with a $C_1$–$C_6$ alkyl group, and include but is not limited to, toluene, xylene, cymene, mixtures thereof, and the like. p-, m-, or o-Cymene is usually the preferred solvent. When p-cymene is employed, the reaction is performed at about 180° C. (the reflux temperature of the mixture) and is typically complete in about 24 hours. Suitable oxidation catalysts include nickel, palladium, platinum, sulfur, selenium, nickel/aluminum oxide, and palladium on carbon. 3%–12% Palladium, most preferably 5%, on carbon is a convenient and preferred oxidant. The oxidizing agent is typically employed in a catalytic fashion but the oxidant/compound of formula VII ratio will vary with the oxidizing agent employed. For example, when 5% palladium on carbon is the oxidant, a 1 to 10, preferably 2 to 4, molar percent of this oxidant, relative to the compound of formula VII, is generally employed. A 3 molar percent is typically most preferred. Yields for this step are typically above 95%.

The skilled artisan will recognize that when starting with a compound of formula VII where R' is oxo, performing the reaction as described above will produce the corresponding compound of formula I where R is hydroxy. Both methods of arriving at the hydroxy compounds of formula I are encompassed within the scope of this invention.

Typically, the compound of formula I is not purified or substantially isolated before its subsequent reaction but is instead converted in situ to compounds of formula VIII as illustrated and described in Scheme 2 below.

Scheme 2

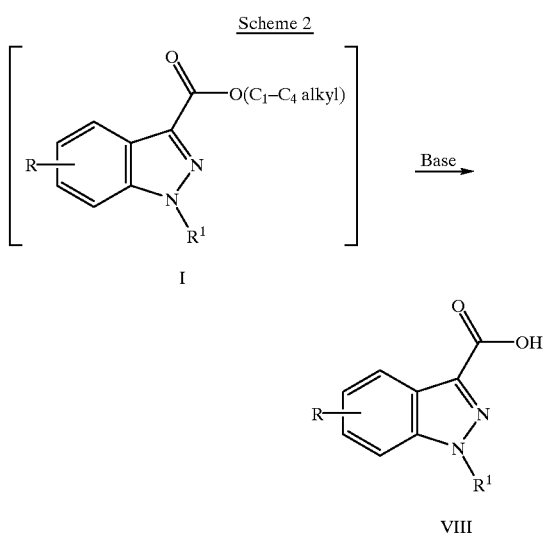

Once it is determined that the oxidation discussed in Scheme 1 is complete, substantial purification of the reaction mixture is not necessary before saponification of the compound of formula I. A simple filtration to remove the oxidation catalyst is normally performed before an aqueous hydroxide base is added directly to the filtrate to afford the compounds of formula VIII. Typically, 1 normal sodium hydroxide is the preferred base. The hydroxide base is typically employed in a molar excess. For example a 1.1 to 3 molar excess, relative to the compound of formula VII is generally employed. A 2 molar excess is typically preferred. The saponification reaction is generally performed at about 95° C. for about 90 minutes. Yields for this step and the overall process of Schemes 1 and 2 are typically above 95%.

Surprisingly, when these lower boiling substituted benzene solvents, relative to the prior art decalin system of 200° C. discussed in the Background of the Invention, are employed, yields become near quantitative in shorter reaction times. In addition, the above process is not limited to a 4-keto starting material and thus substitution at the 4-position of the indazole ring system is readily obtainable. Furthermore, the ability to perform the two step reaction without a substantial purification of the intermediate is desirable for bulk manufacturing of compounds of formula VIII.

Compounds of formula VIII may be converted to compounds of formula IX:

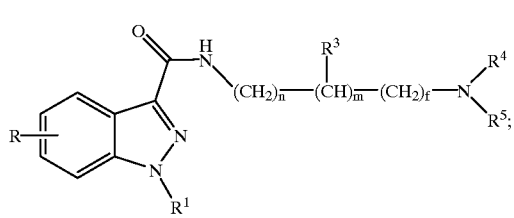

wherein R and $R^1$ are as described supra and m, n, and f are independently 0–5 provided that the sum of m, n, and f is 2–5;
$R^3$ is hydrogen or $C_1$–$C_4$ alkyl;
$R^4$ and $R^5$ combine with the nitrogen to which they are attached to form 1-pyrrolidinyl, 1-piperidinyl, or 1-hexamethyleneiminyl, substituted with phenyl, naphthyl, (phenyl or naphthyl) ($C_1$–$C_3$ alkyl), (phenyl or naphthyl) ($C_1$–$C_3$ alkanoyl), amino, mono- or di($C_1$–$C_4$ alkyl)amino, or a group of the formula $NHYR^6$
wherein a phenyl or naphthyl group is unsubstituted or substituted with 1–3 halo, $C_1$–$C_3$ alkyl or $C_1$–$C_3$ alkoxy groups;
Y is carbonyl, sulfonyl, aminocarbonyl, or oxycarbonyl;
$R^6$ is $C_1$–$C_6$ alkyl, $C_3$–$C_8$ cycloalkyl, $C_6$–$C_{11}$ bicyclo- or tricycloalkyl, (phenyl or naphthyl) ($C_1$–$C_3$ alkyl), phenyl or naphthyl;
wherein a cycloalkyl, bicyclo- or tricycloalkyl group is unsubstituted or substituted with 1–3 hydroxy, halo, or $C_1$–$C_3$ alkoxy groups; or pharmaceutically acceptable salts thereof; by the procedures taught in U.S. U.S. Pat. No. 5,654,320, the teachings of which are herein incorporated by reference.

The compounds of formula IX are useful as potent and selective antagonists of the 5-$HT_4$ receptor.

Compounds of formula X:

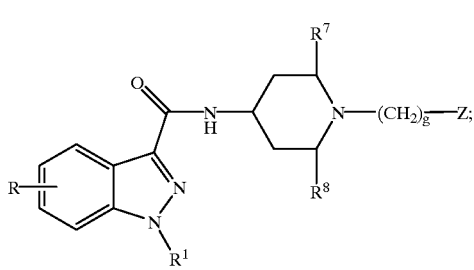

wherein:
R and $R^1$ are as described supra and
g is 1, 2, 3, 4, or 5;
R and $R^1$ are each hydrogen or taken together form a bridge of 1 to 4 methylene units;
Z is OR or $NR^9R^{10}$;
$R^9$ is hydrogen, $C_1$–$C_6$alkyl, $C_3$–$C_6$ cycloalkyl, substituted $C_3$–$C_6$cycloalkyl, phenyl, substituted phenyl, benzoyl, substituted benzoyl, tricyclo[3.3.1.1 $^{3,7}$]decan-1-oyl, or $S(O)_2R^{11}$;
$R^{10}$ is hydrogen or $R^9$ and $R^{10}$ together with the nitrogen to which they are attached form a 1-pyrrolidinyl, 1-piperazinyl, 1,2,3,4-tetrahydro-2-isoquinolinyl, 2,3-dihydro-1-indolinyl, 4-morpholinyl, 1-piperidinyl, 1-hexamethyleneiminyl, or a phthalimidyl ring;
$R^{11}$ is $C_1$–$C_6$ alkyl, $C_3$–$C_6$ cycloalkyl, substituted $C_3$–$C_6$ cycloalkyl, phenyl, or substituted phenyl; or pharmaceutically acceptable salts thereof are also useful as potent and, in some cases, selective antagonists of the 5-$HT_4$ receptor and can be prepared from compounds of formula VIII as discussed in Schemes 3–5 below.

When $R^7$ and $R^8$ form a bridge of 1 to 4 methylene units, the moiety thus formed, in certain cases, can be locked into an endo or exo isomeric form. Both isomers and mixtures thereof are encompassed within the scope of this invention.

When $R^9$ and $R^{10}$ combine with the nitrogen atom to which they are attached to form a heterocyclic group, the heterocyclic group thus formed may be unsubstituted or may be substituted from 1 to 3 times independently with a $C_1$–$C_4$ alkyl group.

Compounds of formula X where Z is $OR^9$ may be prepared from compounds of formula VIII as described in Scheme 3 below where g, R, $R^1$, $R^7$, $R^8$, and $R^9$ are as described supra and $R^{12}$ is a carbonyl activating group.

Scheme 3

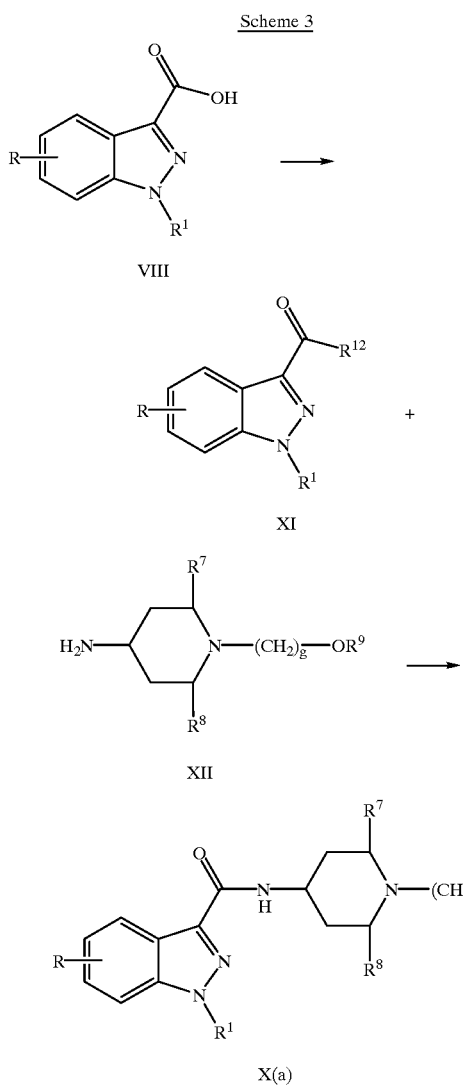

Methods for treating carboxylic acids of formula VIII with activating agents to form compounds of formula XI are discussed below and may be found readily in the literature see, e.g., *The Peptides* reference cited above for such activating reagents.

The next reaction of Scheme 3 is the formation of a carboxamide by coupling the activated carboxylic acid of formula XI and an amine of formula XII. Formation of the amide is readily performed by dissolving or suspending the compound of formula XII in a suitable solvent and adding a compound of formula XI. Tetrahydrofuran, dimethylformamide, or a mixture thereof is usually a convenient and preferred solvent. The compound of formula XI is typically employed in a molar excess. For example, a 1.01 to 1.5 molar excess, relative to the compound of formula XII is generally employed. A 1.25 to 1.4 molar excess is typically preferred. The preferred carbonyl activating group is halo, specifically chloro or bromo. The reaction is typically carried out at a temperature of from about 0° C. to about 60° C., usually preferably at ambient temperature.

As an alternative, the compound of formula XI may be reacted in situ by dissolving or suspending the unactivated compound of formula VIII in a suitable solvent and adding an carbonyl activating reagent. See, e.g., *The Peptides* reference for choices of carbonyl activating reagents. The preferred carbonyl activating reagent is 1,1'-carbonyldiimidazole, but any carbonyl activating agent may be useful. Once the activation is complete, usually in from 30 minutes to about 3 hours when conducted at a temperature of from about room temperature to about 60° C, the compound of formula XII may be added to form the compound of formula X(a). The activating agent and the compound of formula XII are typically employed in a equimolar or slight molar excess. For example, an equimolar to a 1.2 molar excess, relative to the compound of formula VIII or XI is generally employed. A equimolar amount is typically preferred.

Compounds of formula X where Z is $NR^9R^{10}$, $R^9$ is $C_1$–$C_6$ alkyl, $C_3$–$C_6$ cycloalkyl, substituted $C_3$–$C_6$ cycloalkyl, phenyl, or substituted phenyl, and $R^{10}$ is hydrogen, or $R^9$ and $R^{10}$ combine with the nitrogen to which they are attached to form a heterocycle, may be prepared from compounds of formula XI and XIII as described in Scheme 4 where Pg is an amino protecting group, $R^{13}$ is $C_1$–$C_6$ alkyl, $C_3$–$C_6$ cycloalkyl, substituted $C_3$–$C_6$ cycloalkyl, phenyl, or substituted phenyl, and $R^{14}$ is hydrogen, or $R^{13}$ and $R^{14}$ together with the nitrogen to which they are attached form a 1-pyrrolidinyl, 1-piperazinyl, 1,2,3,4-tetrahydro-2-isoquinolinyl, 2,3-dihydro-1-indolinyl, 4-morpholinyl, 1-piperidinyl, 1 hexamethyleneiminyl, or phthalimidyl ring, and g, R, $R^1$, $R^7$, $R^8$, and $R^{12}$ are as described supra.

Scheme 4

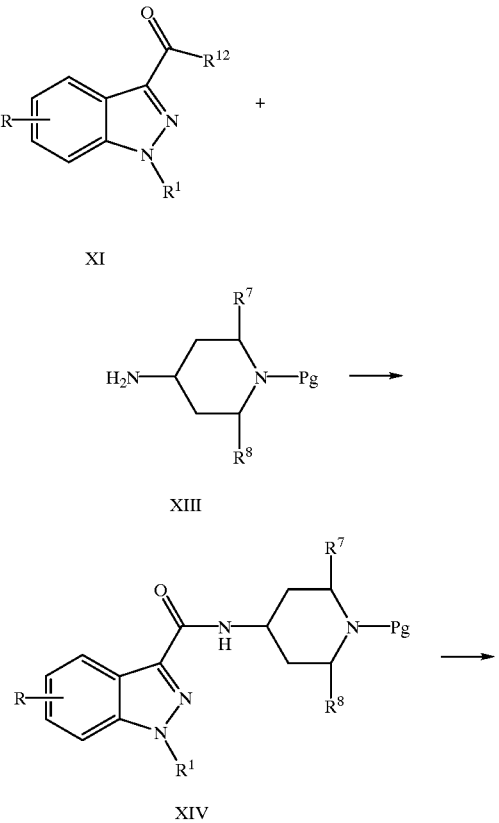

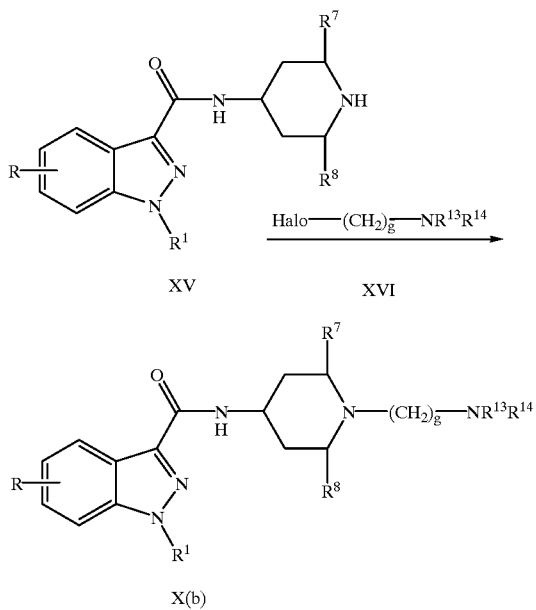

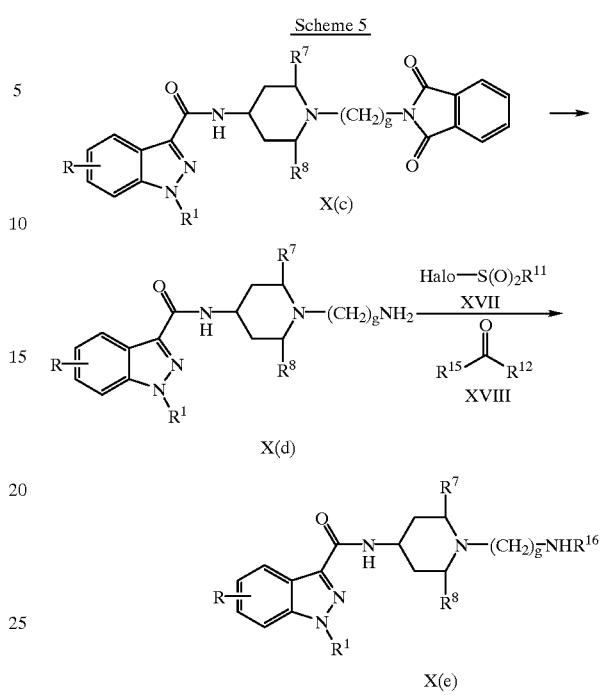

The formation of the carboxamide compound of formula XIV from the activated carboxylic acid of formula XI and an amine of formula XIII may be performed as described in Scheme 3 for the formation of compounds of formula X(a).

Compounds of formula XV may then be prepared by removing the amino protecting group (Pg) from compounds of formula XIV. Choices of protecting groups and methods for their removal may be found in the Barton and Greene references cited above and in the Preparations section which follows.

Compounds of formula X(b) may be prepared by reaction of compounds of formula XV with compounds of formula XVI. For example, a compound of formula XV, typically its hydrochloride salt, dissolved or suspended in a suitable solvent in the presence of a suitable thermodynamic base, may be treated with a compound of formula XVI. Dimethylformamide is usually a convenient and preferred solvent. Typically, sodium carbonate is the preferred thermodynamic base. The thermodynamic base is generally employed in a substantial molar excess. For example a 3 to 5 molar excess, relative to the compound of formula XV is generally employed. A 4 molar excess is typically preferred. The compound of formula XVI is typically and preferably employed in an equimolar amount relative to the compound of formula XV. The reaction is typically carried out at about room temperature when combining the reactants and then at about 100° C. for about 18 hours.

Compounds of formula X where Z is $NR^9R^{10}$, $R^9$ is hydrogen, benzoyl, substituted benzoyl, tricyclo[3.3.1.1$^{3,7}$]decan-1-oyl, or $S(O)_2R^{11}$, and $R^{10}$ is hydrogen, may be prepared from compounds of formula X(b), where $R^{13}$ and $R^{14}$ combine with the nitrogen to which they are attached to form a phthalimidyl ring. This process is shown in Scheme 5 where $R^{15}$ is phenyl, substituted phenyl, or adamant-1-yl, or $S(O)_2R^{11}$, $R^{16}$ is benzoyl, substituted benzoyl, tricyclo[3.3.1.1$^{3,7}$]decan-1-oyl, and g, R, $R^1$, $R^7$, $R^8$, $R^{11}$ and $R^{12}$ are as described supra.

Compounds of formula X(c), prepared as described in Scheme 4, may be converted to other compounds of formula X. For example, compounds of formula X where Z is $NR^9R^{10}$ and $R^9$ and $R^{10}$ are both hydrogen, may be prepared by removing the phthalimidyl amino protecting group from compounds of formula X(c). Methods for the removal of a phthalimidyl amino protecting group may be found in Greene at 358 or in the Preparations section which follows.

Compounds of formula X(d), prepared as described in the preceding paragraph, may also be converted to other compounds of formula X. For example, a compound of formula X(d), dissolved or suspended in a suitable solvent in the presence of a suitable thermodynamic base, may be treated with a compound of formula XVII to yield the compounds of formula X where Z is $NR^9R^{10}$ where $R^9$ is $S(O)_2R^{11}$ and $R^{10}$ is hydrogen. Tetrahydrofuran is usually a convenient and preferred solvent. Typically, triethylamine is the preferred base. The thermodynamic base is typically employed in a slight molar excess. For example a 1.01 to 1.25 molar excess, relative to the compound of formula I(d) is generally employed. A 1.05 molar excess is typically preferred. The compound of formula XVII is typically and preferably employed in an equimolar amount relative to the compound of formula X(d). The reaction is typically carried out at about room temperature for about 18 hours.

Under the same conditions as in the previous paragraph, a compound of formula X(d) may alternatively be treated with a compound of formula XVIII to afford a compound of formula X where Z is $NR^9R^{10}$, $R^9$ is benzoyl, substituted benzoyl, or tricyclo[3.3.1.1$^{3,7}$]decan-1-oyl, and $R^{10}$ is hydrogen.

The $R^1$ substituent (when it is not hydrogen) may be introduced at any convenient point in the reactions of Schemes 1–5. For example, a compound of formula I, VII, VIII, X, X(a)–(c), X(e), XI, or XIV where $R^1$ is hydrogen, dissolved or suspended in a suitable solvent in the presence of a suitable base, may be treated with a compound of the formula $R^1$-halo where halo is preferably bromine or iodine. Dimethylformamide or dimethylsulfoxide is usually a convenient and preferred solvent. When $R^1$ is being installed onto a compound of formula VIII, a suitable base is a hydroxide base, preferably potassium hydroxide. When $R^1$ is being installed onto a compound of formula I, VII, X, X(a)–(c), X(e), XI, or XIV a suitable base is a kinetic base preferably sodium hydride. The hydroxide base is generally and preferably employed in a molar excess relative to the compound of formula VIII, while the kinetic base is generally and preferably employed in an equimolar amount relative to the compound of formula I, VII, X, X(a)–(c), X(e), XI, or XIV. The reaction is typically carried out at about room temperature for about 90 minutes after adding the base and then for from 2 to 18 hours after adding the compound of the formula $R^1$-halo, typically for about 3 hours. These variations on the timing of installing the $R^1$ group are encompassed in the scope of the invention.

The pharmaceutically acceptable salts of the compounds of formula X are typically formed by reacting a compound of formula X with an equimolar or excess amount of acid. The reactants are generally combined in a mutual solvent such as diethylether, tetrahydrofuran, methanol, ethanol, isopropanol, benzene, and the like for acid addition salts. The salts normally precipitate out of solution within about one hour to about ten days and can be isolated by filtration or other conventional methods. For further instruction, see e.g. Berge, S. M, Bighley, L. D., and Monkhouse, D. C., *J. Pharm. Sci.*, 66, 1, 1977.

Acids commonly employed to form pharmaceutically acceptable acid addition salts are inorganic acids such as hydrochloric acid, hydrobromic acid, hydroiodic acid, sulfuric acid, phosphoric acid, and the like, and organic acids such as p-toluenesulfonic, methanesulfonic acid, ethanesulfonic acid, oxalic acid, p-bromophenylsulfonic acid, carbonic acid, succinic acid, citric acid, tartaric acid, benzoic acid, acetic acid, and the like. Preferred pharmaceutically acceptable acid addition salts are those formed with mineral acids such as hydrochloric acid, hydrobromic acid, and sulfuric acid, and those formed with organic acids such as maleic acid, tartaric acid, and methanesulfonic acid.

It should be recognized that the particular counterion forming a part of any salt of the compounds of formula X is not of a critical nature, so long as the salt as a whole is pharmacologically acceptable and the counterion does not contribute undesired qualities to the salt as a whole.

The starting materials for the compounds of formula X may be obtained by a number of routes. For example, compounds of formula XII may be prepared according to the route shown in Scheme 6 where $R^{17}$ is chloro, bromo, or a moiety of the formula O-(hydroxy activating substituent) and g, Pg, $R^7$, $R^8$, and $R^9$ are as described supra.

Scheme 6

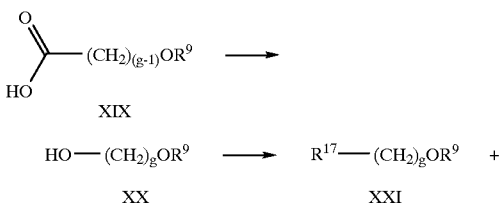

-continued

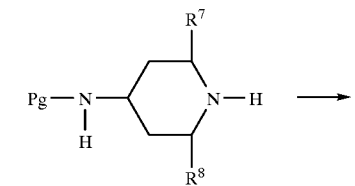

XXII

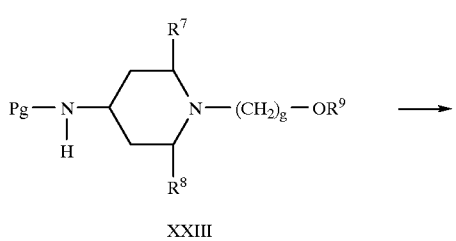

XXIII

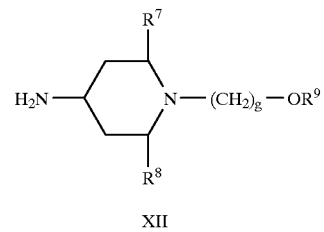

XII

Compounds of formula XX may be prepared from compounds of formula XIX by methods well known in the art. Methods for reducing carboxylic acids to their corresponding alcohols may be found in Larock, *Comprehensive Organic Transformations*, VCH Publishers, Inc., New York, N.Y., 1989, pgs. 548–552. Specifically, a compound of formula XIX, dissolved or suspended in a suitable solvent, may be treated with a reducing agent. Tetrahydrofuran is usually a convenient and preferred solvent. Borane is typically a convenient and preferred reducing agent. The reducing agent is typically employed in a molar excess but the magnitude of the excess will vary with the reducing agent employed. For example, when borane is the reducing agent a 1.1 to a 1.6 molar excess, relative to the compound of formula XIX is generally employed. A 1.35 molar excess is typically preferred. The reaction is typically and preferably performed at about 5° C. when adding the reducing agent then at ambient temperature for about 18 hours.

The alcohol moiety of the resulting product of formula XX may then be converted to a leaving group. For example, a compound of formula XX, dissolved or suspended in a suitable solvent in the presence of a suitable thermodynamic base, may be treated with a hydroxy activating reagent. Pyridine is usually a convenient and preferred solvent and thermodynamic base. A preferred hydroxy activating reagent is p-toluenesulfonyl chloride. The reaction is generally performed at about 5° C. for about 1 to 18 hours.

The leaving group thus installed or formed, i.e. $R^{17}$, in compounds of formula XXI may then be displaced by the amino group of a compound of formula XXII. This may be accomplished by dissolving or suspending a compound of formula XXII in a suitable solvent, in the presence of a suitable thermodynamic base, and adding a compound of formula XXI. Dimethylformamide is usually a convenient and preferred solvent. Typically, sodium carbonate is the preferred thermodynamic base. The thermodynamic base is typically employed in a molar excess. For example a 2 to 6 molar excess, relative to the compound of formula XXII is generally employed. A 3 molar excess is typically preferred. The compound of formula XXI is typically and preferably employed in an equimolar amount relative to the compound of formula XXII. The reaction is typically carried out at about 100° C. for about 18 hours.

Compounds of formula XII may then be obtained by removing the amino protecting group (Pg) from compounds of formula XXIII. Choices of a protecting group and methods for their removal may be found in the Barton and Greene references cited above and in the Preparations section which follows.

Compounds of formula XIII, XVI–XIX, and XXII are known in the art, and, to the extent not commercially available are readily synthesized by standard procedures commonly employed in the art.

Compounds of formula VII may be prepared from commercially available starting materials as described in Snyder, H. R.; Brooks, L. A.; Shapiro, S. H. *Organic Synthesis*, Blatt, A. H., Ed., John Wiley & Sons, New York, 1943; Coll. Vol. II, pg. 531 together with Ainsworth, C. *J. Am. Chem. Soc.* 79, 5242, (1957).

The optimal time for performing the reactions of Schemes 1–6 can be determined by monitoring the progress of the reaction via conventional chromatographic techniques. Furthermore, it is preferred to conduct the reactions of the invention under an inert atmosphere, such as, for example, argon, or, particularly, nitrogen. While choice of solvent is critical for the reactions of Scheme 1 and 2, the choice of solvent in Schemes 3–6 is generally not critical so long as the solvent employed is inert to the ongoing reaction and sufficiently solubilizes the reactants to effect the desired reaction. The compounds of formula VIII, X(b)–X(d), XI, XII, XIV, XV, XX, XXI, and XXIII are preferably isolated and purified before their use in subsequent reactions. These compounds may crystallize out of the reaction solution during their formation and then be collected by filtration, or the reaction solvent may be removed by extraction, evaporation, or decantation. Intermediate and final products of formula X may be further purified, if desired by common techniques such as recrystallization or chromatography over solid supports such as silica gel or alumina.

The following Preparations and Examples are provided to better elucidate the practice of the present invention and should not be interpreted in any way as to limit the scope of same. Those skilled in the art will recognize that various modifications may be made while not departing from the spirit and scope of the invention. All publications mentioned in the specification are indicative of the level of those skilled in the art to which this invention pertains.

PREPARATIONS

Preparation 1

O-(p-Toluenesulfonyl)-3-(4-Fluorophenoxy) propanol

Step 1: Preparation of 3-(4-Fluorophenoxy)propanol 3-(4-Fluorophenoxy)propanoic acid (16.6 g, 90 mmol) was stirred in 100 mL of tetrahydrofuran under a nitrogen atmosphere. The solution was cooled to 5° C. and borane (120 mL, 120 mmol, 1M in tetrahydrofuran) was added dropwise at a rate to keep the temperature of the reaction near 5° C. Once the addition was complete, the solution was allowed to stir at room temperature overnight. The reaction was then cooled below 10° C. and 18 mL of a tetrahydrofuran/water mixture was added. The tetrahydrofuran was removed by evaporation under reduced pressure and the resulting cloudy mixture was diluted with about 200 mL of water. This mixture was extracted three times with diethyl ether. The combined extracts were washed with water, twice with 10% aqueous sodium bicarbonate, and once with brine. The combined extracts were then dried over sodium sulfate, filtered, and concentrated to give 15.24 g of a product oil. Yield: 99%. MS(FD) M+171.

Step 2: Preparation of O-(p-Toluenesulfonyl)-3-(4-Fluorophenoxy)propanol 3-(4-Fluorophenoxy)propanol (7.55 g, 44 mmol) was stirred in 50 mL of pyridine under a nitrogen atmosphere at 5° C. p-Toluenesulfonyl chloride (9.2 g, 50 mmol) was added in one portion and the resulting solution was allowed to stir at 5° C. for 1 hour and then was placed in a refrigerator set at 5° C. overnight. The reaction was then poured into about 300 mL of ice water. This mixture was extracted three times with diethyl ether. The combined extracts were washed 2 times with cold 1N hydrochloric acid and once with cold water. The extracts were then dried over sodium sulfate/potassium carbonate, filtered, and concentrated to give 13.24 g of a solid product. Yield: 93%.

Preparation 2

1-(3-(4-Fluorophenoxy)propyl)-4-Aminopiperidine

Step 1: Preparation of N-Acetyl-1-Benzyl-4-Aminopiperidine

To a solution of 1-benzyl-4-aminopiperidine (19.0 g, 100 mmol) in 300 mL of tetrahydrofuran under a nitrogen atmosphere at room temperature was added triethylamine (15 mL, 105 mmol) followed by a solution of acetyl chloride (7.1 mL, 100 mmol) in 80 mL of tetrahydrofuran keeping the temperature at about 25° C. with the occasional use of an ice bath. The resulting solution was allowed to stir for about 18 hours. The precipitate which formed was filtered and washed with tetrahydrofuran and the filtrate evaporated under reduced pressure to a solid. The solid was recrystallized from about 200 mL of ethyl acetate to give 17.7 g of product. Yield: 76%. EA calculated for $C_4H_{20}N_2O$: C, 72.38; H, 8.68; N, 12.06. Found: C, 72.22; H, 8.64; N, 12.29. MS(FD) M+232.

Step 2: Preparation of N-Acetyl-4-Aminopiperidine

A solution of N-acetyl-1-benzyl-4-aminopiperidine (17.4 g, 75 mmol) and palladium catalyst in ethanol was treated with hydrogen gas. The ethanol was evaporated underreduced pressure to give a solid which was recrystallized from about 120 mL of ethyl acetate to give 6.32 g of product. Yield: 59%. MS(FD) M+142.

Step 3: Preparation of N-Acetyl-1-(3-(4-Fluorophenoxy) propyl)-4-Aminopiperidine N-Acetyl-4-aminopiperidine (5.80 g, 41 mmol) and O-(p-toluenesulfonyl)-3-(4-fluorophenoxy)propanol (13.24 g, 41 mmol) were converted to the title compound by the procedure of Preparation 2, Step 3 to give a crude product which was recrystallized from ethyl acetate to give 7.82 g of the title compound.

Yield: 65%. m.p. 134° C. –136° C. EA calculated for $C_{16}H_{23}N_2O_2F$: C, 65.28; H, 7.88; N, 9.52. Found: C, 65.49; H, 7.91; N, 9.54. MS(FD) M+1 295.

Step 4: Preparation of 1-(3-(4-Fluorophenoxy)propyl)-4-Aminopiperidine

N-Acetyl-1-(3-(4-fluorophenoxy)propyl)-4-aminopiperidine (7.7 g, 26 mmol) was mixed with 50 mL of ethanol and 50 mL of 5N sodium hydroxide. The resulting solution was heated at reflux for about 72 hours. The ethanol was removed and the residue was diluted with water and extracted 3 times with methylene chloride. The extracts were washed with water and brine, dried over sodium sulfate, filtered, and evaporated under reduced pressure to give 5.58 g of an oil.

Yield: 85%. MS(FD) M+252.

EXAMPLES

Example 1

IndazoLe-3-Carboxylic Acid

A mixture of 4,5,6,7-tetrahydroindazole-3-carboxylic acid ethyl ester (21.0 g, 108 mmol), 5% palladium on carbon (7.0 g solid, 3.29 mmol of Pd), and 210 mL of cymene was heated to reflux for 38 hours. At this point complete conversion to the indazole-3-carboxylic acid ethyl ester was shown by TLC (silica gel, 3:1 ethyl acetate-heptane). The reaction was cooled to 120° C. and the 5% palladium on carbon was removed by filtration. The filtrate was combined with 216 mL of 1N sodium hydroxide and tetrabutylammonium hydroxide (1 mL, 1M in methanol). The reaction temperature was maintained at 95° C. for 90 minutes. After cooling to ambient temperature, the phases were separated. The aqueous phase was washed with 50 mL of heptane, then treated with activated carbon (3.0 g) for 30 minutes and filtered. A precipitate formed upon neutralization to pH 4.0 with 6N hydrochloric acid which was collected by filtration. The filter cake was washed with 50 mL of water, then dried in vacuo (50° C., 10 torr) to 17.5 g of product as a white solid.

Yield: 99%. $^1$H NMR (DMSO-d6, 300 MHz) δ 13.8 (br s, 1H), 12.9 (br s, 1H), 8.05 (d, 1H), 7.59 (d, 1H), 7.38 (t, 1H), 7.23 (t, 1H).

Example 2

N-(1-(3-(4-Fluorophenoxy)propyl)piperidin-4-yl)-3-Carboxamido-1H-Indazole

To a solution of 1H-indazole-3-carboxylic acid (645 mg, 4 mmol) in 10 mL of tetrahydrofuran under a nitrogen atmosphere was added 1,1'-carbonyldiimidazole (645 mg, 4 mmol). The resulting solution was allowed to stir at room temperature for 2 hours before a solution of 1-(3-(4-fluorophenoxy)propyl)-4-aminopiperidine (1.00 g, 4 mmol) in 5 mL of tetrahydrofuran was added. The resulting solution was allowed to stir at room temperature for about 18 hours. The tetrahydrofuran was evaporated under reduced pressure and the residue taken up in about 40 mL of methylene chloride. The solution was washed with water, 10% aqueous ammonium hydroxide, and water, dried over sodium sulfate, filtered, and evaporated under reduced pressure to give a dark red gum. The crude product was purified by flash chromatography (silica gel, methylene chloride:methanol:ammonium hydroxide 100:5:0.5) to give 680 mg of product.

Yield: 43%. m.p. 196° C.–198° C. EA calculated for $C_{22}H_{25}N_4O_2F$: C, 66.65; H, 6.36; N, 14.13. Found: C, 66.44; H, 6.45; N, 14.04. MS(FD) M+396.

Example 3

N-(1-(3-(4-Fluorophenoxy)propyl)piperidin-4-yl)-1-Isopropyl-3-Carboxamido-1H-Indazole Hydrochloride To a solution of N-(1-(3-(4-fluorophenoxy)propyl) piperidin-4-yl)-3-carboxamido-1H-indazole (540 mg, 1.36 mmol) in 10 mL of dimethylformamide under a nitrogen atmosphere was added sodium hydride (60% dispersion in mineral oil, 55 mg, 1.36 mmol). The resulting mixture was allowed to stir at room temperature for 1 hour before cooling briefly and adding 2-iodopropane (0.17 mL, 1.63 mmol). The resulting solution was allowed to stir at room temperature for about 18 hours. The dimethylformamide was evaporated under reduced pressure and the residue taken up in methylene chloride. The methylene chloride was washed with 10% aqueous sodium carbonate, water, and brine, dried over sodium sulfate, filtered, and evaporated under reduced pressure to give a red oil. The oil was dissolved in ethanol and one equivalent of concentrated hydrochloric acid was added (0.144 mL). The solution was concentrated to a residue which was stirred in diethyl ether to precipitate the product. The product was collected by filtration then recrystallized from ethyl acetate/methanol to give 406 mg.

Yield: 63%. m.p. 174° C.–175° C. EA calculated for $C_{25}H_{32}N_4O_2FCl$: C, 63.21; H, 6.79; N, 11.79. Found: C, 63.50; H, 6.90; N, 11.82. MS(FD) M+438 (free base).

Representative compounds of formula X have been biologically tested to demonstrate their interaction with the 5-$HT_4$ receptor. The test was carried out in esophagus smooth muscle, freshly removed from male Wistar rats weighing 250 g–300 g each. The rats were euthanized by cervical dislocation, and the esophagus was removed and dissected free of connective tissue. The esophagi were used as longitudinal preparations, obtaining two preparations from each animal. The tissues were tied with thread at each end with the lower end being tied to a stationary glass rod and the upper end to a force transducer.

Tissues were mounted in organ baths containing 10 mL of modified Krebs' solution of the following composition (millimolar) NaCl 118.2; KCl 4.6; $CaCl_2 2H_2O$ 1.6; $KH_2PO_4$ 1.2; $MgSO_4$ 1.2; dextrose 10.0; and $NaHCO_3$ 24.8. Tissue bath solutions were maintained at 37° C. and aerated with 95% $O_2$/5% $CO_2$. Tissues were placed under optimum resting force, 1 g, and were allowed to equilibrate for 1 hour before exposure to drugs. Isometric contractions were recorded as changes in grams of force on the Modular Instruments Inc. (Malvern, Pa.) model M4000™ data acquisition system with Sensotec (Columbus, Ohio) model MBL 5514-02™ transducers.

For studies with partial agonists or antagonists, tissues were preincubated with vehicle or antagonist for 45 minutes. All drugs were prepared daily in deionized water and kept on ice during the course of the experiment. The tissues were contracted by incubation with $10^{-7}M–10^{-5}M$ carbamylcholine, and were relaxed by the addition of serotonin at $10^{-8}M–10^{-10}M$, which treatment relaxed the tissue and reduced the contraction caused by carbamylcholine. Addition of a representative compound of formula X antagonized the serotonin response and reduced the observed relaxations of the tissue. Repeated tests of each compound at various concentrations were carried out and the representative compounds of formula X reduced the observed relaxations at concentrations of 10 μmol or less. This reduction demonstrates that the representative compounds of formula X have high affinity for the 5-$HT_4$ receptor.

Furthermore, it is also remarkable that compounds of formula X are markedly more potent in their affinities at the 5-$HT_4$ receptor than in other activities and, for some of the compounds at other receptors; the selectivity is often shown by concentration differences amounting to two or even more orders of magnitude to achieve the same binding potency.

Accordingly, the compounds of formula X are very potent in affecting the 5-$HT_4$ receptor, and particularly in providing an antagonist effect at that receptor. Thus, the improved process for preparing compounds of formula IX and X embodied in this invention is valuable.

I claim:

1. A process for preparing a compound of the formula:

[structure of compound I(a) parent: indazole-3-carboxamide-N-ethyl-piperidinyl-adamantanecarboxamide with N1-isopropyl]

consisting of:

a) oxidizing a compound of formula VII(a):

[structure VII(a): 4,5,6,7-tetrahydro-1-isopropyl-indazole-3-carboxylic acid C1–C4 alkyl ester]

by heating a mixture of a compound of formula VII(a), a substituted benzene solvent, and an oxidation catalyst at a temperature between 110° C. and the reflux temperature of the mixture to form a compound of formula I(a):

[structure I(a): 1-isopropyl-indazole-3-carboxylic acid C1–C4 alkyl ester]

b) optionally filtering the resulting reaction mixture from step a);

c) adding a suitable base to the resulting reaction mixture of step a) or to the filtrate of step b) to form a compound of the formula VIII(a):

[structure VIII(a): 1-isopropyl-indazole-3-carboxylic acid]

d) optionally reacting the compound of formula VIII(a) with a carbonyl activating reagent to provide a compound of the formula:

[structure XI(a): 1-isopropyl-indazole-3-carbonyl-R13]

wherein $R^{12}$ is a carbonyl activating group; and e) reacting the compound of formula VIII(a) or the compound of formula XI(a) with an amine of the formula

[structure: H2N-ethyl-piperidinyl-NH-adamantanecarboxamide]

2. A process according to claim 1 wherein the oxidation catalyst is palladium.

3. A process according to claim 2 wherein the palladium catalyst is palladium on carbon wherein the percentage of palladium in the palladium on carbon is between 3% and 12%.

4. A process according to claim 3 wherein the molar percent of oxidation catalyst relative to the compound of formula VII is between 1% and 10%.

5. A process according to claim 4 wherein the molar percent is between 2% and 4%.

6. A process according to claim 5 wherein the substituted benzene solvent is independently disubstituted.

7. A process according to claim 6 wherein the substituted benzene solvent is ortho, meta, or para cymene.

8. A process according to claim 7 wherein the oxidation is performed at a temperature between 170° C. and the reflux temperature of the mixture.

9. A process according to claim 7 wherein the solvent is para-cymene and the oxidation is performed at the reflux temperature of the mixture.

10. A process according to claim 9 wherein the oxidation is performed for from 20–40 hours.

11. A process according to claim 10 wherein the oxidation is performed for from 22–26 hours.

12. A process according to claim 1 wherein the compound of formula I is a compound wherein the $C_1$–$C_4$ ester group at the 3-position of the indazole is a methyl or ethyl ester.

* * * * *